United States Patent
Böhm et al.

[11] Patent Number: 6,063,181
[45] Date of Patent: May 16, 2000

[54] 1,7-DISUBSTITUTED PERYLENE-3,4,9, 10-TETRACARBOXYLIC ACIDS, THEIR DIANHYDRIDES AND DIIMIDES OF SAID ACIDS

[75] Inventors: Arno Böhm, Mannheim; Harald Arms, Worms; Georg Henning; Peter Blaschka, both of Ludwigshafen, all of Germany

[73] Assignee: BASF Aktiengesellschaft, Ludwigshafen, Germany

[21] Appl. No.: 09/091,263

[22] PCT Filed: Dec. 11, 1996

[86] PCT No.: PCT/EP96/05525

§ 371 Date: Jun. 18, 1998

§ 102(e) Date: Jun. 18, 1998

[87] PCT Pub. No.: WO97/22608

PCT Pub. Date: Jun. 26, 1997

[30] Foreign Application Priority Data

Dec. 18, 1995 [DE] Germany ............ 195 47 210

[51] Int. Cl.[7] ............ C09B 3/14; C07D 493/06
[52] U.S. Cl. ............ 106/493; 549/232; 252/301.17; 252/301.32
[58] Field of Search ............ 549/232; 106/287.21, 106/493; 252/301.17, 301.32

[56] References Cited

U.S. PATENT DOCUMENTS 5,677,417 10/1997 Muellen et al. ............ 528/310

*Primary Examiner*—John Kight
*Assistant Examiner*—Charanjit S. Aulakh
*Attorney, Agent, or Firm*—Oblon, Spivak, McClelland, Maier & Neustadt, P.C.

[57] ABSTRACT

1,7-Disubstituted perylene-3,4,9,10-tetracarboxylic dianhydrides I and perylere-3,4,9,10-tetracarboxylic acids Ia

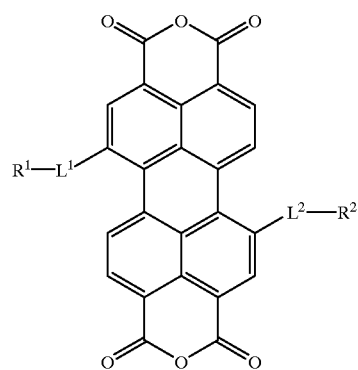

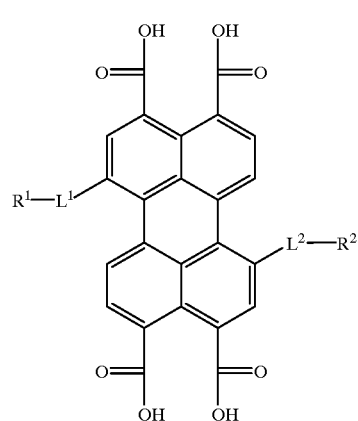

where $L^1$, $L^2$ independently of one another are 1,2-ethylene, 1,2-ethenylene and 1,2-ethynylene, and $R^1$, $R^2$ independently of one another are hydrogen or substituted or unsubstituted $C_1$–$C_{30}$-alkyl, their preparation and use as pigments, laser dyes and precursors for preparing fluorescent dyes, polymeric colorants, pigments and pigment additives, and also 1,7-disubstituted perylene-3,4,9,10-tetracarboxylic diimides (VI) as their intermediates.

11 Claims, No Drawings

1,7-DISUBSTITUTED PERYLENE-3,4,9,10-TETRACARBOXYLIC ACIDS, THEIR DIANHYDRIDES AND DIIMIDES OF SAID ACIDS

CROSS-REFERENCE TO RELATED APPLICATIONS

The present application is a 371 continuation of PCT/EP96/05525 filed Dec. 11, 1996, now WO 97/22608 published Jun. 26, 1997.

BACKGROUND OF THE INVENTION

1. Field of the Invention

The present invention relates to 1,7-disubstituted perylene-3,4,9,10-tetracarboxylic dianhydrides. perylene-3, 4,9,10-tetracarboxylic dianhydrides of the general formula I and perylene-3,4,9,10-tetracarboxylic acids of the general formula Ia

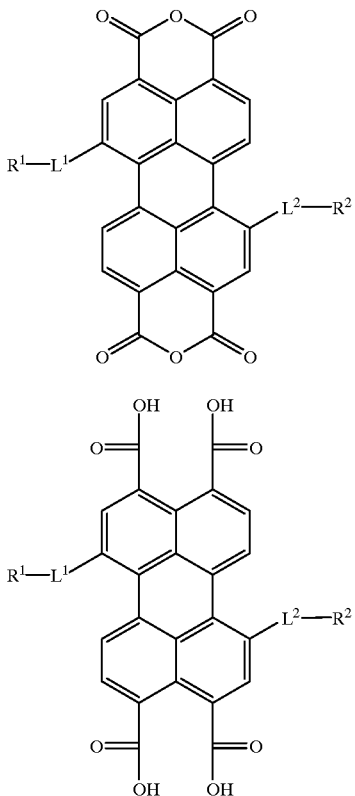

where

L$^1$ and L$^2$ independently of one another are 1,2-ethylene, 1,2-ethenylene and 1,2-ethynylene;

R$^1$ and R$^2$ independently of one another are hydrogen or C$_1$–C$_{30}$-alkyl, whose carbon chain can be interrupted by one or more groups —O—, —S—, —NR$^3$-, —CO— and/or —SO$_2$— and/or which can be substituted one or more times by —COOR$^3$, —SO$_3$R$^3$, hydroxyl, cyano, C$_1$–C$_6$-alkoxy, C$_5$–C$_8$-cycloalkyl or aryl or by a 5- to 7-membered heterocyclic radical which is attached via a nitrogen atom and can include further heteroatoms and/or can be aromatic, R$^3$ being hydrogen or C$_1$–C$_6$-alkyl, and to a process for preparing the perylene-3,4,9,10-tetracarboxylic dianhydrides (I) or the acids (1a) and to their use as pigments, laser dyes and precursors for preparing fluorescent dyes, polymeric colorants, pigments and pigment additives.

The invention additionally relates to novel 1,7-disubstituted perylene-3,4,9,10-tetracarboxylic diimides of the general formula VI

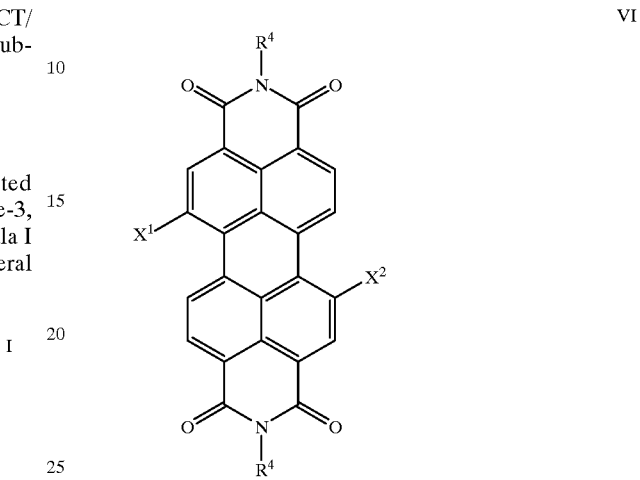

where

X$^1$ is bromine or is —L—R, where
L is 1,2-ethylene, 1,2-ethenylene or 1,2-ethynylene and
R is hydrogen or C$_1$–C$_{30}$-alkyl whose carbon chain can be interrupted by one or more groups —O—, —S—, —NR$^3$—, —CO— and/or —SO$_2$— and/or which can be substituted one or more times by —COOR$^3$, —SO$_3$R$^3$, hydroxyl, cyano, C$_1$–C$_6$-alkoxy, C$_5$–C$_8$-cycloalkyl or aryl or by a 5- to 7-membered heterocyclic radical which is attached via a nitrogen atom and can include further heteroatoms and/or can be aromatic, R$^3$ being hydrogen or C$_1$–C$_6$-alkyl;

X$^2$ is bromine or —L—R;

R$^4$ is C$_4$–C$_{30}$-alkyl whose carbon chain can be interrupted by one or more groups —O—, —S— or —CO—, or is C$_5$–C$_8$-cycloalkyl or aryl which can be substituted one or more times by C$_1$–C$_6$-alkyl or C$_1$–C$_6$-alkoxy, as intermediates for the perylene-3,4,9,10-tetracarboxylic dianhydrides (I) or the acids (Ia), and to a process for preparing the perylene-3,4,9,10-tetracarboxylic diimides (VI).

Perylene-3,4,9,10-tetracarboxylic acids and their anhydrides are known to be important intermediates for preparing perylimide pigments and perylimide dyes, but are also useful themselves for coloring or pigmenting high molecular mass organic materials.

In addition to unsubstituted perylene-3,4,9,10-tetracarboxylic acid, which can be obtained by hydrolyzing perylene-3,4,9,10-tetracarboxylic diimide in concentrated sulfuric acid at about 200° C., there is particular interest in perylene-tetracarboxylic acids which are substituted in the perylene skeleton and whose properties in use, such as solubility, inherent color and fluorescence, can be tailored by introducing suitable substituents.

WO-A-94/255 discloses 1,6,7,12-tetraaroxy-substituted perylene-3,4,9,10-tetracarboxylic dianhydrides prepared by alkaline hydrolysis of the corresponding diimides in a polar protic solvent. The tetraaroxy-substituted diimides themselves are obtained by reacting the tetrachlorinated diimides with arylates (EP-A-227 980).

1,7-disubstituted perylene-3,4,9,10-tetracarboxylic acids, such as the novel compounds (Ia) which, like all perylene-3,4,9,10-tetracarboxylic acids, are generally in the form of the dianhydrides, have not been disclosed to date. In addition, the dihalogenated perylene-3,4,9,10-tetracarboxylic diimides described in EP-A-39 912 and in DE-A-412 122 are always mixtures of products with differing degrees of halogenation (especially tetra-, tri- and monohalogenated products); it has not been possible to prepare the dihalogenated diimides specifically.

It is therefore an object of the invention to provide novel 1,7-disubstituted perylene-3,4,9,10-tetracarboxylic acids and dianhydrides.

We have found that this object is achieved by the 1,7-disubstituted perylene-3,4,9,10-tetracarboxylic dianhydrides and the corresponding acids of the above-defined formulae I and Ia (referred to below as dianhydrides I), which may be substituted symmetrically or asymmetrically.

Preferred dianhydrides I are the subject of the subclaim.

We have also discovered a process for preparing the symmetric dianhydrides I, which comprises a) reacting-1,7-dibromoperylene-3,4,9,10-tetracarboxylic dianhydride (II) or 1,7-dibromoperylene-3,4,9,10-tetracarboxylic acid (IIa) in the presence of a polar aprotic solvent and in the presence or absence of an imidation catalyst with a primary amine of the general formula III

$R^4$—$NH_2$   III where $R^4$ is $C_4$–$C_{30}$-alkyl whose carbon chain can be interrupted by one or more groups —O—, —S— or —CO—, or is $C_5$–$C_8$-cycloalkyl or aryl which can be substituted one or more times by $C_1$–$C_6$-alkyl or $C_1$–$C_6$-alkoxy, b) reacting the 1,7-dibromoperylene-3,4,9,10-tetracarboxylic diimide formed in step a), of the general formula IV

IV

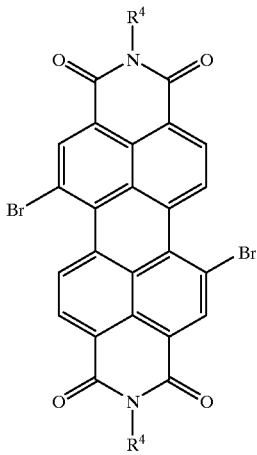

in the presence of an aprotic solvent, a palladium complex as catalyst, a copper salt as cocatalyst and a base with a 1-alkyne of the general formula V

H—C≡C—$R^1$   V in a molar ratio of from 1:2 to 1:4, and c) hydrolyzing the symmetric, 1,7-disubstituted perylene-3,4,9,10-tetracarboxylic diimides, formed in step b), of the general formula VI'

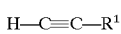

VI'

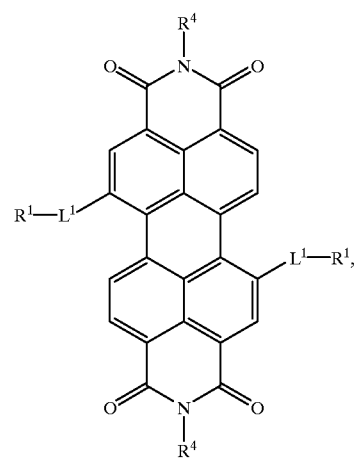

after additional reduction of the unsaturated bonds in $L^1$, if desired, in the presence of a polar protic solvent and a base to form the symmetric dianhydrides I.

We have also discovered a process for preparing the asymmetric dianhydrides I, which corresponds to the process for preparing the symmetric dianhydrides I in step a) but in which the 1,7-dibromoperylene-3,4,9,10-tetracarboxylic diimides IV are reacted in step b)—which is likewise carried out in the presence of an aprotic solvent, a palladium complex as catalyst, a copper salt as cocatalyst and a base—first with a 1-alkyne of the general formula Va H—C≡C—$R^1$   Va

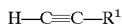

and then with a different 1-alkyne of the general formula Vb

H—C≡C—$R^2$   Vb

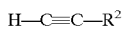

in each case in a molar ratio of from 1:1 to 1:2 and the resulting asymmetric 1,7-disubstituted perylene-3,4,9,10-tetracarboxylic diimides of the general formula VI"

VI"

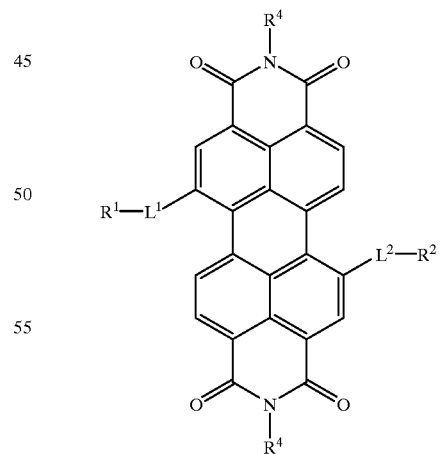

are then hydrolyzed, in step c), after additional reduction of the unsaturated bonds in $L^1$ and $L^2$, if desired, in the presence of a polar protic solvent and a base to form the asymmetric dianhydrides I.

We have, furthermore, discovered the 1,7-disubstituted perylene-3,4,9,10-tetracarboxylic diimides of the above-defined formula VI (referred to as perylimides VI), which can likewise be symmetrically or asymmetrically substituted, as intermediates for the dianhydrides I, and processes for preparing the perylimides VI which comprise steps a) and b) of the process for preparing the corresponding dianhydrides I.

Preferred perylimides VI are the subject of the subclaim.

Yet further, we have discovered the use of the dianhydrides I as pigments, laser dyes and precursors for preparing fluorescent dyes, polymeric colorants, pigments and pigment additives.

Finally, we save also discovered the use of the perylimides VI as pigments and dyes for coloring high molecular mass organic materials and inorganic materials, as laser dyes, and as organic materials for electroluminescence applications.

Each alkyl in the formulae I (including Ia), III, IV, V (including Va and Vb) and VI (including VI' and VI") can be either straight-chain or branched. Substituted aromatic radicals can generally, have up to three, preferably one or two, of the substituents stated.

Specific examples of suitable radicals $R^1$ and $R^2$ (and of their substituents; in addition to hydrogen are:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl tetradecyl, pentadecyl, hexadecyl, heptadecyl, octadecyl, nonadecyl and eicosyl (the above designations isooctyl, isononyl, isodecyl and isotridecyl are trivial names and derive from the alcohols obtained by the oxo synthesis—cf. in this context Ullmanns Encyklopadie der technischen Chemie, 4th edition, volume 7, 215–217, and volume 11, 435 and 436);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-(N-methylamino)- and 2-(N-ethylamino)ethyl, 2-(N,N-dimethylamino)ethyl, 2- and 3-(N,N-dimethylamino) propyl, 3-(N-isopropylamino)propyl, 2- and 4-(N-propylamino)butyl, 2- and 4-(N,N-dimethylamino)butyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

methylcarboxymethyl, ethylcarboxymethyl, propylcarboxymethyl, butylcarboxymethyl, pentylcarboxymethyl, hexylcarboxymethyl, methyl-2-carboxyethyl, ethyl-2-carboxyethyl, propyl-2-carboxyethyl, butyl-2-carboxyethyl, pentyl-2-carboxyethyl, hexyl-2-carboxyethyl, methyl-3-carboxypropyl, ethyl-3-carboxypropyl, propyl-3-carboxypropyl, butyl-3-carboxypropyl, pentyl-3-carboxypropyl, hexyl-3-carboxypropyl, methyl-4-carboxybutyl, methyl-5-carboxypentyl, methyl-6-carboxyhexyl, methyl-8-carboxyoctyl, methyl-10-carboxydecyl, methyl-12-carboxydodecyl and methyl-14-carboxytetradecyl; sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

methylsulfomethyl, ethylsulfomethyl, propylsulfomethyl, butylsulfomethyl, pentylsulfomethyl, hexylsulfomethyl, methyl-2-sulfoethyl, ethyl-2-sulfoethyl, propyl-2-sulfoethyl, butyl-2-sulfoethyl, pentyl-2-sulfoethyl, hexyl-2-sulfoethyl, methyl-3-sulfopropyl, ethyl-3-sulfopropyl, propyl-3-sulfopropyl, butyl-3-sulfopropyl, pentyl-3-sulfopropyl and hexyl-3-sulfopropyl, methyl-4-sulfobutyl, methyl-5-sulfopentyl, methyl-6-sulfohexyl, methyl-8-sulfooctyl, methyl-10-sulfodecyl, methyl-12-sulfododecyl and methyl-14-sulfotetradecyl;

2-hydroxyethyl, 2- and 3-hydroxypropyl, 1-hydroxyprop-2-yl, 2- and 4-hydroxybutyl, 1-hydroxybut-2-yl and 8-hydroxy-4-oxaoctyl, 2-cyanoethyl, 3-cyanopropyl, 2-methyl-3-ethyl-3-cyanopropyl, 7-cyano-7-ethylheptyl and 4-methyl-7-methyl-7-cyanoheptyl;

methoxy, ethoxy, propoxy, isopropoxy, butoxy, isobutoxy, tert-butoxy, pentoxy, isopentoxy, neopentoxy, tert-pentoxy and hexoxy;

cyclopentyl, cyclohexyl, cycloheptyl, cyclooctyl, 2-dioxanyl, 4-morpholinyl, 2- and 3-tetrahydrofuryl, 1-, 2- and 3-pyrrolidinyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazo2yl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 1-isoquinolyl.

Examples of particularly preferred radicals —L—R (including —$L^1$—$R^1$ and —$L^2$—$R^2$) are ethenyl and ethynyl which are unsubstituted or substituted by $C_1$–$C_{18}$-alkyl, especially $C_4$–$C_8$-alkyl, which can itself be substituted, especially terminally (in position ω) by cyano, hydroxyl, carboxyl, methylcarboxy or ethylcarboxy. Specific examples are:

ethynyl, 1-propynyl, 1-butynyl, 1-pentynyl, 3-methyl-1-butynyl, 1-hexynyl, 3- and 4-methyl-1-pentynyl, 3,3-dimethyl-1-butynyl, 1-heptynyl, 3-, 4- and 5-methyl-1-hexynyl, 3,3-, 3,4- and 4,4-dimethyl-1-pentynyl, 3-ethyl- 1-pentynyl, 1-octinyl, 3-, 4-, 5- and 6-methyl-1-heptynyl, 3,3-, 3,4-, 3,5-, 4,4- and 4,5-dimethyl-1-hexynyl, 3-, 4- and 5-ethyl-1-hexynyl, 3-ethyl-3-methyl-1-pentynyl, 3-ethyl-4-methyl-1-pentynyl, 3,3,4- and 3,4,4-trimethyl-1-pentynyl, 1-nonynyl, 1-decynyl, 1-undecynyl and 1-dodecynyl;

4-cyano-1-butynyl, 5-cyano-1-pentynyl, 6-cyano-1-hexynyl, 7-cyano-1-heptynyl and 8-cyano-1-octynyl;

4-hydroxy-1-butynyl, 5-hydroxy-1-pentynyl, 6-hydroxy-1-hexynyl, 7-hydroxy-1-heptynyl, 8-hydroxy-1-octynyl, 9-hydroxy-1-nonynyl, 10-hydroxy-1-decynyl, 11-hydroxy-1-undecynyl and 12-hydroxy-1-dodecynyl;

4-carboxy-1-butynyl, 5-carboxy-1-pentynyl, 6-carboxy-1-hexynyl, 7-carboxy-1-heptynyl, 8-carboxy-1-octynyl, 4-methylcarboxy-1-butynyl, 5-methylcarboxy-1-pentynyl, 6-methylcarboxy-1-hexynyl, 7-methylcarboxy-1-heptynyl, 8-methylcarboxy-1-octynyl, 4-ethylcarboxy-1-butynyl, 5-ethylcarboxy-1-pentynyl, 6-ethylcarboxy-1-hexynyl, 7-ethylcarboxy-1-heptynyl and 8-ethylcarboxy-1-octynyl;

ethenyl, 1-propenyl, 1-butenyl, 1-pentenyl, 3-methyl-1-butenyl, 1-hexenyl, 3- and 4-methyl-1-pentenyl, 3,3-dimethyl-1-butenyl, 1-heptenyl, 3-, 4- and 5-methyl-1-hexenyl, 3,3-, 3,4- and 4,4-dimethyl-1-pentenyl, 3-ethyl-1-pentenyl, 1-octenyl, 3-, 4-, 5- and 6-methyl-1-heptenyl, 3,3-, 3,4-, 3,5-, 4,4- and 4,5-dimethyl-1-hexenyl, 3-, 4-, and 5-ethyl-1-hexenyl, 3-ethyl-3-methyl-1-pentenyl, 3-ethyl-4-methyl-1-pentenyl, 3,3,4- and 3,4,4-trimethyl-1-pentenyl, 1-nonenyl, 1-decenyl, 1-undecenyl und 1-dodecenyl;

4-cyano-1-butenyl, 5-cyano-1-pentenyl, 6-cyano-1-hexenyl, 7-cyano-1-heptenyl and 8-cyano-1-octenyl;

4-hydroxy-1-butenyl, 5-hydroxy-1-pentenyl, 6-hydroxy-1-hexenyl, 7-hydroxy-1-heptenyl, 8-hydroxy-1-octenyl, 9-hydroxy-1-nonenyl, 10-hydroxy-1-decenyl, 11-hydroxy-1-undecenyl and 12-hydroxy-1-dodecenyl;

4-carboxy-1-butenyl, 5-carboxy-1-pentenyl, 6-carboxy-1-hexenyl, 7-carboxy-1-heptenyl, 8-carboxy-1-octenyl, 4-methylcarboxy-1-butenyl, 5-methylcarboxy-1-pentenyl, 6-methylcarboxy-1-hexenyl, 7-methylcarboxy-1-heptenyl, 8-methylcarboxy-1-octenyl, 4-ethylcarboxy-1-butenyl, 5-ethylcarboxy-1-pentenyl, 6-ethylcarboxy-1-hexenyl, 7-ethylcarboxy-1-heptenyl and 8-ethylcarboxy-1-octenyl.

Suitable examples of $R^3$ are hydrogen and the abovementioned $C_1$–$C_6$-alkyls.

Suitable examples of $R^4$ are the abovementioned $C_4$–$C_{30}$-alkyls, those interrupted by —O—, —S— or —CO—, and $C_5$–$C_8$-cycloalkyls and aryls, for example naphthyl and, in particular, phenyl, which can be substituted by 1, 2 or 3 of the $C_1$–$C_6$-alkyls or $C_1$–$C_6$-alkoxys stated, such as 2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropyl-3,5 phenyl, 2,4,5-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5 and 2,6-diisobutylphenyl, 2,4,6-triisobutylphenyl, 2-, 3- und 4-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl.

The novel preparation of the dianhydrides I is a multistage synthesis. In step a) 1,7-dibromoperylene-3,4,9,10-tetracarboxylic dianhydride (II) is reacted with a primary amine III to form the corresponding 1,7-dibromoperylene-3,4,9,10-tetracarboxylic diimide IV, which in step b) is reacted with a 1-alkyne V (or stepwise with different 1-alkynes Va and Vb) to form the perylimide VI, which finally in step c) is hydrolyzed under basic conditions, after additional reduction of the unsaturated bond in the bridge member L, if desired, to form the dianhydride I.

The starting product for the novel preparation process, 1,7-dibromoperylene-3,4,9,10-tetracarboxylic dianhydride (II), can be obtained by selective bromination of perylene-3,4,9,10-tetracarboxylic dianhydride in 100% by weight sulfuric acid (monohydrate).

An expedient procedure comprises first of all stirring perylene-3,4,9,10-tetracarboxylic dianhydride in the sulfuric acid for 2–6 hours and then heating this mixture, after adding a halogenation catalyst such as iodine (preferably 30–40 mmol per mole of anhydride) to the reaction temperature (generally 80–90° C.). At this point the bromine is added slowly dropwise (usually over 6–10 hours), using preferably 2–2.5 mol of bromine ($Br_2$) per mole of anhydride. After cooling to room temperature and displacing the unreacted bromine by nitrogen, water is added, a little at a time, in order to reduce the concentration of sulfuric acid to about 85–88% by weight.

Working up the reaction mixture to the 1,7-dibromoperylene-3,4,9,10-tetracarboxylic dianhydride (II) can be carried out by filtering off the precipitated product, washing it with 85–88% by weight sulfuric acid, stirring it into water, filtering the mixture again, washing the product with water and then drying it.

Step a) of the novel preparation process, the reaction of the 1,7-dibromoperylene-3,4,9,10-tetracarboxylic dianhydride (II) with the primary amine, is carried out in the presence of a polar aprotic solvent and in the presence or absence of an imidation catalyst.

Suitable polar aprotic solvents for this step are, in particular, aprotic nitrogen heterocycles such as pyridine, pyrimidine, quinoline, isoquinoline, quinaldine, N-methylpiperidine, N-methylpiperidone and, in particular, N-methylpyrrolidone.

The quantity of solvent used is not critical per se and is usually 5–20 kg, preferably 10–15 kg, per kg of (II).

Suitable imidation catalysts include organic and inorganic acids, for example formic acid, acetic acid, propionic acid and phosphoric acid, which are preferably employed in highly concentrated form, and also organic and inorganic solvents of transition metals such as zinc, iron and copper and of magnesium, for example zinc acetate, zinc propionate, zinc oxide, iron(II) acetate, iron(III) chloride, iron(II) sulfate, copper(II) acetate, copper(II) oxide and magnesium acetate. Of course it is also possible to use mixtures of these catalysts.

The presence of an imidation catalyst is particularly advisable when reacting aromatic amines and is also advantageous when reacting cycloaliphatic amines, whereas for short-chain aliphatic amines no catalyst is usually required.

5–80% by weight of catalyst based on (II) is generally employed. With the organic acids, preferred quantities are 50–80%, and with the transition metal salts and magnesium salts they are 10–40% by weight, based in each case on (II).

Primary amines which can be employed in the novel preparation process are all those which are stable under the reaction conditions and which, with perylene-3,4,9,10-tetracarboxylic dianhydrides, form diimides which can be hydrolyzed under basic conditions.

Examples of particularly preferred primary amines III are stearylamine, 5-nonylamine, cyclopentylamine, cyclohexylamine, cycloheptylamine, aniline, 4-methylaniline, 4-ethylaniline, 4-tert-butylaniline, 3,5-dimethylaniline, 3,5-diethylaniline and 3,5-di-tert-butylaniline.

The molar ratio of amine III to (II) is normally from about 2:1 to 4:1, preferably from about 2.2:1 to 3:1.

Step a) is generally carried out at 40–180° C. 60–100° C. is the preferred range when reacting aliphatic and cycloaliphatic amines, and 120–160° C. when reacting aromatic amines.

It is advisable to work under an inert-gas atmosphere (for example using nitrogen).

Step a) of the novel process can be carried out at atmospheric pressure or under superatmospheric pressure at, normally, up to 10 bar. The use of superatmospheric pressure is especially expedient when working with volatile amines (boiling point $\leq$ about 180° C.)

The reaction is normally over after 2–10 hours, especially 4–7 hours.

The specific procedure for step a) is expediently as follows:

1,7-Dibromoperylene-3,4,9,10-tetracarboxylic dianhydride (II), solvent and, if used, catalyst are charged to the reactor, the amine III is: added at room temperature with stirring, the apparatus is flushed with nitrogen for about 15 minutes, and the mixture is heated with stirring to the reaction temperature and held there for about 4–7 hours. After cooling to room temperature, the reaction product is filtered off, washed with an aliphatic alcohol such as methanol and dried.

When working under superatmospheric pressure, the reaction vessel used is a pressure apparatus to which a nitrogen pressure of about 1–2 bar is applied after the components have been introduced, which are then heated at the reaction temperature for the desired period and then cooled, after which the reactor is let down.

For further purification the resulting 1,7-dibromoperylene-3,4,9,10-tetracarboxylic diimide IV can be dissolved in a halogenated hydrocarbon such as methylene chloride, chloroform or tetrachloroethane, the solution can be filtered over silica gel and the filtrate can be concentrated to dryness. The purity of the diimide IV thus treated is usually >98% and it can therefore be used directly for the subsequent reactions.

Step b) of the novel preparation process, the reaction of the 1,7-dibromoperylene-3,4,9,10-tetracarboxylic diimide IV with the 1-alkyne V, is carried out in the presence of an aprotic solvent, a palladium complex as catalyst, a copper salt as cocatalyst and a base.

Suitable solvents in this step include linear and cyclic aliphatic ethers having up to 10 carbon atoms, such as diethyl ether, di-n-propyl ether, di-n-butyl ether, 1,2-dimethoxyethane, 1,2-diethoxyethane, dioxane and in particular, tetrahydrofuran.

The quantity of solvent employed is not critical per se and is usually 30–100 kg, preferably 40–60 kg, per kg of diimide IV.

The base which is added serves simultaneously as cosolvent. Bases particularly suitable for this purpose are organic nitrogen bases which can be mixed with the ethers and have a melting point below room temperature and a boiling point above the reaction temperature.

Preferred bases are aliphatic amines having up to 15 carbon atoms, especially tertiary amines such as triethylamine, tri-n-propylamine and tri-n-butylamine, and cycloaliphatic amines such as, in particular, piperidine.

0.2–1.5 kg, preferably 0.8–1.2 kg, of base are usually added per kg of solvent.

The catalysts used are palladium complexes which are employed in conjunction with copper (I) salts as cocatalysts.

Examples of suitable palladium complexes are tetrakis (tris-o-tolylphosphine)palladium(0), [1,2-bis (diphenylphosphino)ethane]palladium(II) chloride, [1,1'-bis (diphenylphosphino)ferrocene]palladium(II) chloride, bis (triethylphosphine)palladium(II) chloride, bis (tricyclohexylphosphine)palladium(II) chloride, bis (triphenylphosphine)palladium(II) acetate, (2,2'-bipyridyl) palladium(II) chloride and, in particular, tetrakis (triphenylphosphine)palladium(0), bis(triphenylphosphine) palladium(II) chloride, bis(acetonitrile)palladium(II) chloride and bis(benzonitrile)palladium(II) chloride.

Examples of particularly suitable copper(I) salts are copper(I) iodide and copper(I) bromide.

In general 2–15 mol-%, preferably 5–10 mol-%, of palladium complex and generally 2–20 mol-%, preferably 7–12 mol-%, of copper(I) salt are employed, based in each case on the diimide IV.

The reaction temperature in step b) is usually 20–140° C., especially 40–90° C.

Depending on the alkyne employed the reaction can be carried out at atmospheric pressure or under superatmospheric pressure, at, normally, up to 50 bar. The use of superatmospheric pressure is necessary when working with volatile alkynes such as acetylene.

When symmetric perylimides VI (VI') are prepared, the molar ratio of the starting compounds, diimide IV and alkyne V, is generally from 1:2 to 1:5, preferably from 1:2 to 1:4.

When preparing asymmetric perylimides VI (VI"), when first of all only one of the two bromine atoms in the perylene skeleton is replaced by the reaction with an alkyne Va and then the second bromine atom is replaced by the reaction with a different alkyne Vb, the molar ratio of diimide IV to alkyne V is generally in each case from 1:1 to 1:2, preferably from 1:1 to 1:1.5.

The reaction forming the symmetric perylimides VI' is usually over after 1–15 hours, in particular 2–10 hours. In contrast, the preparation of the monosubstituted monobromoperylimide as an intermediate in the reaction to form the asymmetric perylimides VI" generally takes only 15–60 minutes, in particular 15–30 minutes. The subsequent reaction forming the disubstituted perylimide VI" is then subject to the reaction time specified for the symmetric perylimides VI'.

Depending on the chosen reaction conditions, step b) of the novel preparation process may produce perylimides VI comprising 1,2-ethynylenes or 1,2-ethenylenes as bridge member L.

To prepare perylimides VI comprising unsaturated bridge members, it is advisable to work under inert gas (for example argon or nitrogen). If reaction is carried out for more than 4 hours and/or at more than 100° C., the acetylenic bond is reduced directly to the ethylenic bond.

Perylimides VI comprising ethylene radicals L can be obtained by subsequently stirring the reaction mixture in a hydrogen atmosphere. However, it is also possible to carry out subsequent reduction of the unsaturated bond using, for example, hydrogen with catalysis by palladium on active charcoal in a procedure which is customary for such reductions (cf. Larock, Comprehensive Organic Transformations, VCH Publishers New York, 1989, 6–17; March, Advanced Organic Chemistry, John Wiley and Sons New York, 4th Edition 1992, 775–777; Journal of Organic Chemistry, Volume 45, 4926–4931 (1980)).

The specific procedure in step b) for preparing the symmetric perylimides VI' is expediently as follows:

A stirred solution or suspension of the diimide IV in a mixture of solvent and base (both anhydrous as far as possible) is charged to the reactor, the suspension is saturated with nitrogen by repeated degassing and gassing with dry nitrogen, the copper(I) salt, the palladium complex and the 1-alkyne V are introduced in a nitrogen countercurrent (volatile alkylenes such as acetylene are weighed out and introduced in gaseous form into the closed apparatus), and the reaction mixture is heated at the desired reaction temperature for the desired period ($\leq$4 h or >4 h). Then, if desired, gaseous hydrogen is introduced and the mixture is stirred at the reaction temperature for a further 4–8 hours. Subsequently (after letting down the reactor beforehand if appropriate) the reaction mixture is introduced directly, ie. without being cooled, with vigorous stirring into about three times the volume of a mixture of approximately equal parts by weight of concentrated hydrochloric acid and ice, and the crude product is filtered off, washed with half-concentrated hydrochloric acid until the washings are colorless and then with water until the washings are neutral, and dried.

For further purification the resulting perylimide VI can be recrystallized with appropriate solvents such as, for example, halogenated hydrocarbons such as methylene chloride, chloroform or tetrachloroethane, or cyclic ethers such as dioxane or tetrahydrofuran, or can be chromatographed over a short silica gel column, in which case the abovementioned solvents or mixtures thereof, depending on the functionality of R, can be used as eluent.

To prepare the asymmetric perylimides VI" the specific procedure is expediently as already described for the symmetric perylimides VI' except that first of all the reduced quantity of 1-alkyne Va is added and the mixture is then heated at the desired reaction temperature for 15–30 minutes. The monosubstituted monobromoperylimide VI can then be first isolated as described above or else reacted directly with the second 1-alkyne Vb by stirring at the desired reaction temperature for 2–4 hours or more.

The working up of the reaction mixture and subsequent purification of the crude product can of course be carried out as described above for the symmetric perylimides VI'.

The perylimides VI treated in this way usually have a purity of >98% and can be employed directly for the subsequent reactions. However, they can also be used themselves as valuable pigments and dyes.

Step c) of the novel process, the hydrolysis of the perylimide VI to form the dianhydride I, is carried out (after reduction of the perylimide beforehand, if appropriate) in the presence of a polar protic solvent and a base.

Particularly suitable polar protic solvents for this step are $C_1$–$C_{10}$-alkanols such as ethanol, propanol, n-butanol, tert-butanol, 2-methyl-2-butanol, n-hexanol, n-decanol and, preferably, isopropanol. In order to accelerate hydrolysis it is expedient to add water as well, generally 0.1–0.2 mol per millimol of perylimide VI.

The quantity of solvent employed is not critical per se and is usually 50–200 kg, preferably 60–80 kg, per kg of perylimide VI.

Particularly suitable bases are alkali metal hydroxides, such as sodium hydroxide and potassium hydroxide, which are generally employed in amounts of 4–10 kg, preferably 5–7 kg, per kg of perylimide VI.

The reaction temperature in step c) is usually 20–140° C., in particular 40–90° C.

The hydrolysis is normally over after 3–10 hours, in particular 4–6 hours.

The specific procedure in step c) of the novel preparation process is Expediently as follows:

A mixture of perylimide VI, solvent and base is heated at the desired reaction temperature for 4–6 hours and cooled to room temperature, and the crude product which has precipitated in the course of cooling is filtered off and washed with an alcohol, such as isopropanol or propanol, until the washings are colorless. For further purification, the resulting dianhydride I is expediently introduced into 30–100 times the quantity of dilute inorganic acid, for example 5–10% by weight hydrochloric acid, boiled up briefly and filtered after cooling, and the product is washed with water to neutrality and dried.

The novel preparation process can be used to obtain the 1,7-disubstituted perylene-3,4,9,10-tetracarboxylic dianhydrides I in a technically simple and economic process in high purities (generally >95%) and good yields.

The novel dianhydrides I are advantageously useful for pigmenting printing inks, coating compositions, especially daylight-fluorescent colors, and plastics, as laser dyes and precursors for preparing fluorescent dyes, polymeric colorants, pigments and pigment additives.

The novel perylimides VI can also be used with advantage as pigments and dyes for coloring high molecular mass organic materials and inorganic materials, as laser dyes and as organic materials for electroluminescence applications.

EXAMPLES

A) Preparation of 1,7-dibromoperylene-3,4,9,10-tetracarboxylic dianhydride (II)

Example 1

A mixture of 292.5 g (0.75 mol) of perylene-3,4,9,10-tetracarboxylic dianhydride (purity>98%) and 4420 g of 100% by weight sulfuric acid was stirred for 12 hours at room temperature, 7 g of iodine were then added, and it was heated to 85° C. Subsequently, 262.5 g (1.64 mol) of bromine were added dropwise over 8 hours.

The reaction mixture was cooled to room temperature, the excess bromine was displaced by nitrogen and then the concentration of sulfuric acid was reduced to 86% by weight by adding a total of 670 g of water, a little at a time, over 1 hour. During this addition the reaction mixture heats up to 85° C. again: it was cooled and the precipitated product was filtered off over a G4 glass frit, washed with 3 kg of 86% by weight sulfuric acid and then stirred up in 5 l of water; the mixture was filtered again and the product was washed to neutrality and dried under reduced pressure at 120° C.

370 g of II were obtained in the form of a bright red finely crystalline powder with a melting point>360° C. and a purity of >98%, corresponding to a yield of 90%.

Analytical data:

Elemental analysis (% by weight calc./found): C: 52.4/52.1; H: 1.1/1.1; O: 17.45/17.4; Br: 29.1/29.4; IR (KBr): ν=1782+1770 (s, C=O), 1735+1723 (s, C=O) cm$^{-1}$; UV/VIS (H$_2$SO$_4$): $\lambda_{max}$ (ε)=408 (10309), 520 (29410), 554 (43141) nm.

B) Preparation of 1,7-dibromoperylene-3,4,9,10-tetracarboxylic diimides IV

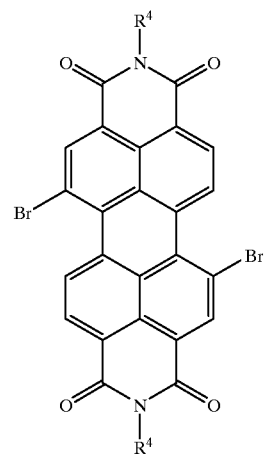

IV

Examples 2 and 3

First a g of the imidation catalyst K and then, a little at a time, a total of 381 mmol of the primary amine R$^4$-NH$_2$ (III)

were added with stirring to a mixture of 69.9 g (127 mmol) of 1,7-dibromoperylene-3,4,9,10-tetracarboxylic dianhydride (II) (Example 1) in 900 ml of N-methylpyrrolidone. The reaction mixture was then heated under nitrogen to the reaction temperature T°C. at which it was stirred for 6 hours.

After cooling to room temperature the precipitated reaction product was filtered off, washed with a total of 2 l of methanol and dried under reduced pressure at 100° C.

Further details regarding these experiments and their results are collated in Table 1.

Analytical data:

Elemental analysis (% by weight calc./found): C: 63.5/63.3; H: 3.2/3.2; N: 3.7/3.7; O: 8.5/8.6; Br: 21.1/21.2; Mass (FD): m/z=754 (M$^+$, 100%); IR (KBr): ν=1696 (s, C=O), 1653 (s, C=O) cm$^{-1}$; UV/VIS (CHCl$_3$): $\lambda_{max}$ (ε)=485 (29214), 532 (45100) nm.

TABLE 1

| | | | | | | Result | | | |
|---|---|---|---|---|---|---|---|---|---|
| Example | R$^4$ | a g | | Catalyst K | T [° C.] | Yield [g]/[%] | Purity [%] | Appearance | m.p. [° C.] |
| 2 | Cyclohexyl | 42.8 | | Glacial acetic acid | 85 | 75.1/83 | 97 | bright red, microcrystalline | >360 |
| 3 | 3,5-Dimethyl-phenyl | 17.5 | | Zinc acetate | 140 | 83.8/87 | 96 | magenta, crystalline | >360 |

Example 2a

For further purification, 65.3 g of the N,N'-dicyclohexyl-1,7-dibromoperylene-3,4,9,10-tetracarboxylic diimide (IVa) from Example 2 was stirred in 800 ml of methylene chloride for 1 hour and then filtered over a 1 l G4 glass frit which was filled to 2/3 of its capacity with silica gel (0.063–0.2 mm particle size; methylene chloride as eluent).

Evaporation of the filtrate to remove the methylene chloride under reduced pressure gave 58 g of IVa as an orange-red crystalline powder with a purity>99%.

Analytical data:

Elemental analysis (% by weight calc./found): C: 60.7/60.6; H: 4.0/4.0; N: 3.9/3.9; O: 9.0/9.0; Br: 22.4/22.3; IR (KBr): ν=1698 (s, C=O), 1655 (s, C=O) cm$^{-1}$; UV/VIS (CHCl$_3$) : $\lambda_{max}$ (ε)=491 (33962), 526 (50478) nm.

Example 3a

By a method similar to that of Example 2a, 80 g of the N,N'-bis(3',5'-dimethylphenyl)-1,7-dibromoperylene-3,4,9,10-tetracarboxylic diimide (IVb) from Example 3 were purified using hot tetrachloroethane as eluent.

75 g of IVb were obtained as a bright red crystalline powder with a purity>98%.

C) Preparation of 1,7-disubstituted perylene-3,4,9,10-tetracarboxylic diimides VI

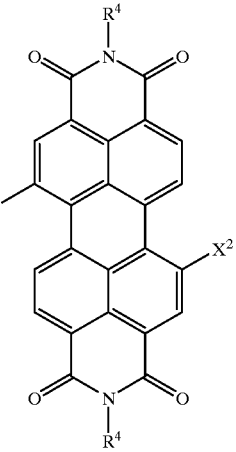

VI

Examples 4 to 10

2.45 mmol of the purified 1,7-dibromoperylene-3,4,9,10-tetracarboxylic diimide (IV) from Example 2a and, respectively, 3a were introduced with stirring and in nitrogen countercurrent into a mixture of 100 ml of absolute tetrahydrofuran and 100 ml of freshly distilled piperidine (Examples 4 to 6 and 9 to 10) or 100 ml of triethylamine (Examples 7 and 8), then 45 mg (0.23 mmol) of copper(I) iodide, 225 mg (0.19 mmol) of tetrakis(triphenylphosphine) palladium(0) and b mg (b' mmol) of the 1-alkyne V were added in succession, and the mixture was heated at 80° C. under nitrogen for t hours (Examples 4 to 6 and 9 to 10) or 60° C. (Examples 7 and 8).

The resulting black-violet (Example 9: dark green) reaction mixture was cooled to room temperature and then introduced with stirring into 600 ml of half-concentrated hydrochloric acid. The precipitated reaction product was washed first with 400 ml of half-concentrated hydrochloric acid and then to neutrality with water and dried under reduced pressure at 100° C.

The crude product was dissolved in 80 ml of methylene chloride and chromatographed over silica gel (0.063–0.2 mm particles size) using methylene chloride as eluent (column 330×100 mm).

Further details regarding these experiments and their results are collated in Table 2.

Analytical data for Example 9:

Elemental analysis (% by weight calc./found): C: 70.7/71.3; H: 5.2/5.3; N: 3.9/4.1; O: 9.0/8.7; Br: 11.2/10.6; Mass (FD): m/z=712/714 ($M^+$, $^{79}Br/^{81}Br$, 100%) IR (KBr):

TABLE 2

| Ex. | $X^1$ | $X^2$ | $R^4$ | a g | Diimide IV from Ex. | b mg | b' mmol | Alkyne V | t h | Yield [g]/[%] | Purity [%] | Appearance | Softening point [° C.] |
|---|---|---|---|---|---|---|---|---|---|---|---|---|---|
| 4 | 1-Hexenyl | ≡$X^1$ | Cyclohexyl | 1.74 | 2a | 508 | 6 | 1-Hexyne | 8 | 0.89/50 | >98 | dark violet, amorphous | 70 |
| 5 | 1-Hexynyl | ≡$X^1$ | Cyclohexyl | 1.74 | 2a | 508 | 6 | 1-Hexyne | 4 | 1.05/60 | >98 | black-violet, crystalline | 62 |
| 6 | 5-Cyano-1-pentynyl | ≡$X^1$ | Cyclohexyl | 1.74 | 2a | 560 | 6 | 5-Hexyne-nitrile | 4 | 1.12/62 | >98 | black-violet, amorphous | 71 |
| 7 | 1-Dodecynyl | ≡$X^1$ | Cyclohexyl | 1.74 | 2a | 1627 | 9.8 | 1-Dodecyne | 10 | 1.76/81 | >98 | black-violet, amorphous | 88 |
| 8 | 3-Acetoxy-3-methyl-1-butynyl | ≡$X^1$ | Cyclohexyl | 1.74 | 2a | 1236 | 9.8 | 2-Methyl-3-butyne-2-acetate | 10 | 1.34/68 | >98 | dark red, crystalline | 237 |
| 9 | 1-Hexynyl | Br | Cyclohexyl | 1.74 | 2a | 288 | 3.4 | 1-Hexyne | 0.5 | 0.98/56 | >98 | dark green, lustrous, crystalline | 225 |
| 10 | 1-Hexenyl | ≡$X^1$ | 3,5-Dimethylphenyl | 1.86 | 3a | 508 | 6 | 1-Hexyne | 8 | 1.01/54 | >98 | dark red, crystalline | 122 |

Analytical data for Example 4:

Elemental analysis (% by weight calc./found): C: 80.2/80.0; H: 7.0/7.1; N: 3.9/3.8; O: 8.9/9.1; Mass (FD): m/z=718 ($M^+$, 100%); IR (KBr): $\nu$=1696 (s, C=O), 1650 (s, C=O) cm$^{-1}$; UV/VIS (CHCl$_3$): $\lambda_{max}$ ($\epsilon$)=286 (22906), 342 (12569), 398 (10544), 442 (9515), 469 (17094), 540 (12179) nm.

Analytical data for Example 5:

Elemental analysis (% by weight calc./found): C: 80.6/79.8; H: 6.5/6.7; N: 3.9/3.8; O: 8.95/9.6; Mass (FE): m/z=714 ($M^+$, 100%); IR (KBr): $\lambda$=2210 (w, C≡C), 1695 (s, C=O), 1649 (s, C=O) cm$^{-1}$; UV/VIS (CHCl$_3$): $\lambda_{max}$ ($\epsilon$)=293 (31542), 403 (15601), 441 (7321), 471 (11359), 538 (26011) nm.

Analytical data for Example 6:

Elemental analysis (% by weight calc./found): C: 78.2/77.7; H: 5.5/5.6; N: 7.6/7.5; O: 8.7/9.1; Mass (FD): m/z=736 ($M^+$, 100%); IR (KBr): $\nu$=2238 (m, C≡N), 1698 (s, C=O), 1653 (s, C=O) cm$^{-1}$; UV/VIS (CHCl$_3$): $\lambda_{max}$ ($\epsilon$)=292 (30108), 403 (15831), 442 (6913), 472 (12003), 540 (24631) nm.

Analytical data for Example 7:

Elemental analysis (% by weight calc./found): C: 81.6/81.5; H: 8.0/8.0; N: 3.2/3.2; O: 7.25/7.3; Mass (FI)): m/z=882 ($M^+$, 100%); IR (KBr): $\nu$=2206 (w, C≡C) , 1695 (s, C=O) , 1650 (s, C=O cm$^{-1}$; UV/VIS (CHCl$_3$): $\lambda_{max}$ ($\epsilon$)=285 (17642), 294 (19311) , 471 (6729), 505 (12936), 543 (21103) nm.

Analytical data for Example 8:

Elemental analysis (% by weight calc./found): C: 74.8/74.6; H: 5.75/5.8; N: 3.5/3.5; O: 15.95/16.1; Mass (FIDO): m/z=802 ($M^+$, 100%); IR (KBr): $\nu$=2209 (w, C≡C), 1741 (s, C=O, ester), 1695 (s, C=O), 1650 (s, C=O) cm$^{-1}$; UV/VIS (CHCl$_3$): $\lambda_{max}$ ($\epsilon$)=288 (19733), 293 (21004) , 473 (6610), 514 (14263), 565 (25317) nm.

$\nu$=1690 (s, C=O), 1652 (s, C=O) cm$^{-1}$; UV/VIS (CHCl$_3$): $\lambda_{max}$ ($\epsilon$)=448 (11950), 629 (15300) nm.

Analytical data for Example 10:

Elemental analysis (% by weight calc./found): C: 81.9/81.7; H: 6.0/6.1; N: 3.7/3.7; O: 8.4/8.5: Mass (FD): m/z =762 ($M^+$, 100%); IR (KBr): $\nu$=1694 (s, C=O), 1649 (s, C=O) cm$^{-1}$; UV/VIS (CHCl$_3$): $\lambda_{max}$ ($\epsilon$)=290 (25703), 339 (8112), 401 (10291), 458 (15388), 559 (23900) nm.

Example 11

By a method similar to that indicated above, 0.8 g (1.12 mmol) of the N,N'-dicyclohexyl-1-hexynyl-7-bromoperylene-3,4,9,10-tetracarboxylic diimide from Example 9 was reacted with 0.14 g (1.5 mmol) of 5-hexynenitrile in 4 hours.

After purification by column chromatography, 0.52 g of N,N'-dicyclohexyl-1-hexynyl-7-(5'-cyanopentynyl) perylene-3,4,9,10-tetracarboxylic diimide ($X^1$: 1-hexynyl; $X^2$: 5-cyano-1-pentynyl) was obtained in the form of a black-violet microcrystalline powder having a softening point of 83° C. and a purity of 98%, corresponding to a yield of 64%.

Analytical data:

Elemental analysis (% by weight calc./found): C: 79.4/79.2; H: 6.0/6.1; N: 5.8/5.8; O: 8.8/8.9; Mass (FD)): m/z=725 ($M^+$, 100%); IR (KBr): $\nu$=2236 (m, C≡N), 1695 (s, C=O), 1650 (s, C=O) cm$^{-1}$; UV/VIS (CHCl$_3$): $\lambda_{max}$ ($\epsilon$)=293 (31542), 403 (15601), 441 (7321), 471 (11359), 538 (26011) nm.

Example 12

1.0 g (1.4 mmol) of the N,N'-dicyclohexyl-1,7-dihexenylperylene-3,4,9,10-tetracarboxylic diimide from Example 4 were dissolved in 150 ml of methanol, 0.5 g of a commercial hydrogenation catalyst (5% palladium on active charcoal) was added, and the mixture was hydrogenated at room temperature under a hydrogen pressure of 1 bar.

After removal of the catalyst by filtration and of the solvent by distillation, 0.92 g of N,N'-dicyclohexyl-1,7-dihexylperylene-3,4,9,10-tetracarboxylic diimide ($x^1=x^2=$ hexyl) was obtained in the form of a black-red, amorphous powder having a softening point of 112° C. and a purity of 98%, corresponding to a yield of 91%.

Analytical data:

Elemental analysis (% by weight calc./found): C: 79.75/79.7; H: 7.55/7.5; N: 3.85/3.8; O: 8.85/8.9; Mass (FE): m/z=722 (M$^+$, 100%); IR (KBr): $\nu$=1695 (s, C=O), 1650 (s, C=O) cm$^{-1}$; UV/VIS (CHCl$_3$): $\lambda_{max}$ ($\epsilon$)=278 (19712), 339 (11823), 398 (7210), 463 (8132), 510 (20101), 554 (29300) nm.

D) Preparation of 1,7-disubstituted perylene-3,4,9,10-tetracarboxylic dianhydrides I

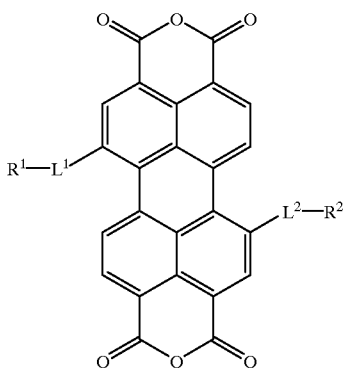

Example 13

A mixture of 10 g of the N,N'-dicyclohexyl-1,7-dihexenylperylene-3,4,9,10-tetracarboxylic diimide from Example 4, 1 l of isopropanol, 65 g of potassium hydroxide and 26 g of water was refluxed for 5 hours.

After cooling to room temperature, the precipitated reaction product was filtered off, washed with isopropanol until the washings were colorless, then introduced with stirring into 1 l of 10% by weight hydrochloric acid and heated briefly at boiling. After cooling to room temperature, the product was again filtered off, washed to neutrality with water and dried under reduced pressure at 100° C.

6.8 g of 1,7-dihexenylperylene-3,4,9,10-tetracarboxylic dianhydride ($L^1=L^2$=1,2-ethylene, $R^1=R^2$=n-butyl) were obtained as a dark red amorphous powder with a melting point>360° C. and a purity>98% (determined by UV/VIS spectroscopy and semiquantitative thin-layer chromatography on silica gel using trichloroacetic acid/toluene as mobile phase), corresponding to a yield of 88%.

Example 14

By a method similar to that of Example 13, 10 g of the N,N'-bis (3',5'-dimethylphenyl)-1,7-dihexenylperylene-3,4,9,10-tetracarboxylic diimide from Example 10 were reacted.

6.2 g of 1,7-dihexenylperylene-3,4,9,10-tetracarboxylic dianhydride were obtained of the same quality as in Example 13, corresponding to a yield of 85%.

Analytical data for Examples 13 and 14:

Elemental analysis (% by weight calc./found): C: 77.7/177.6; H: 5.1/5.1; O: 17.2/17.3; IR (KBr): $\nu$=1769 (s, C=O), 1722 (s, C=O) cm$^{-1}$; UV/VIS (CHCl$_3$): $\lambda_{max}$ ($\epsilon$)=399 (12732), 532 (46311) nm.

We claim:

1. A 1,7-disubstituted perylene-3,4,9,10-tetracarboxylic dianhydride of formula I

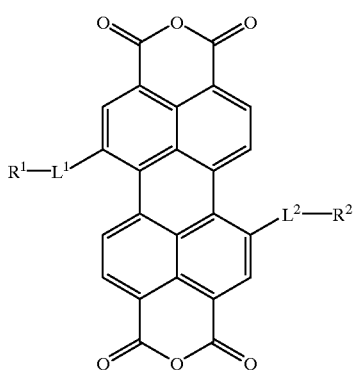

wherein $L^1$, $L^2$ independently of each other are 1,2-ethylene, 1,2-ethenylene or 1,2-ethynylene;

$R^1$, $R^2$ independently of each other are hydrogen or $C_1$–$C_{30}$-alkyl, whose carbon atom chain optionally is interrupted by at least one moiety selected from the group consisting of —O—, —S—, —NR$^3$—, —CO— and —SO$_2$— and/or which is optionally substituted once by a moiety selected from the group consisting of —COOR$^3$, —SO$_3$R$^3$, cyano or a 5- to 7-membered heterocyclic radical which is attached via a nitrogen atom and which optionally contains one additional nitrogen atom, oxygen atom or sulfur atom and which is optionally aromatic; or substituted one or two times by hydroxyl, $C_1$–$C_5$-alkoxy, $C_5$–$C_8$-cycloalkyl or aryl, $R^3$ being hydrogen or $C_1$–$C_6$-alkyl.

2. A compound as claimed in claim 1, where $L^1$, $L^2$ are identical and are 1,2-ethenylene or 1,2-ethynylene and $R^1$, $R^2$ independently of one another are hydrogen or $C_1$–$C_{18}$-alkyl which can be substituted by —COOR$^3$, hydroxyl or cyano.

3. The 1,7-disubstituted perylene-3,4,9,10-tetracarboxylic dianhydride of claim 1, wherein said heterocyclic radical is 4-morpholinyl 1-pyrrolidinyl, 1-piperidyl or 4-piperidyl.

4. A process for preparing a symmetrical compound of formula I as claimed in claim 1 or 2, wherein $R^1$ and $R^2$ and $L^1$ and $L^2$ are each identical, which comprises:

a) reacting 1,7-dibromoperylene-3,4,9,10-tetracarboxylic dianhydride (II)

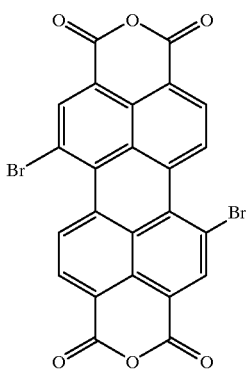

II in the presence of a polar aprotic solvent with a primary amine of formula III

III wherein $R^4$ is $C_4$–$C_{30}$-alkyl, whose carbon atom chain optionally is interrupted by at least one moiety selected from the group consisting of —O—, —S— or —CO—, or is a $C_5$–$C_8$-cycloalkyl or aryl which optionally is substituted by at least one $C_1$–$C_6$-alkyl or $C_1$–$C_6$-alkoxy group, b) reacting the 1,7-dibromoperylene-3,4,9,10-tetracarboxylic diimide of step a) of formula IV

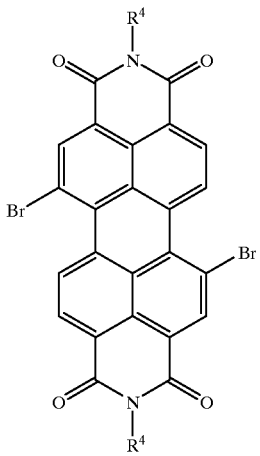

in the presence of an aprotic solvent, a palladium complex as a catalyst, a copper salt as a cocatalyst and a base with a 1-alkyne of formula V

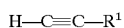

V in a molar ratio of from 1:2 to 1:4; and c) hydrolyzing the symmetrical 1,7-disubstituted perylene-3,4,9,10-tetracarboxylic diimide formed in step (b) of formula VI'

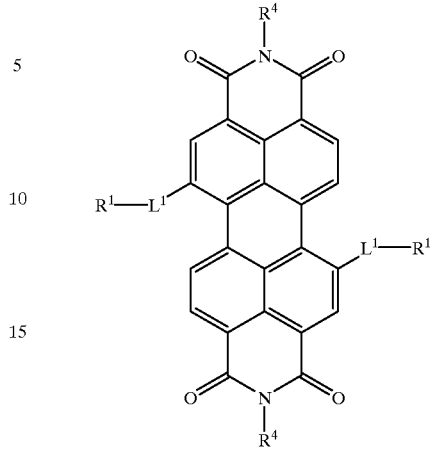

VI' in the presence of a polar aprotic solvent and a base to form the symmetric 1,7-disubstituted perylene-3,4,9,10-tetracarboxylic dianhydride (I).

5. The process of claim 4, wherein, in step (a), the imidation reaction is conducted in the presence of a catalyst.

6. The process of claim 4, which comprises, in step (c), prior to hydrolysis, reducing the unsaturated bonds in substituent $L^1$.

7. A process for preparing an asymmetric compound of formula (I) as claimed in claim 1 or 2, wherein $R^1$ and $R^2$ are different and $L^1$ and $L^2$ are identical or different, which comprises:

a) reacting 1,7-dibromoperylene-3,4,9,10-tetracarboxylic dianhydride (II)

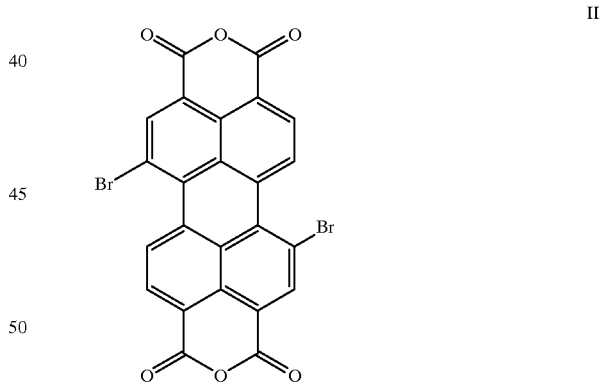

II in the presence of a polar aprotic solvent with a primary amine of formula III

III wherein $R^4$ is $C_4$–$C_{30}$-alkyl whose carbon chain optionally is interrupted by at least one moiety selected from the group consisting of —O—, —S— or —CO— or is a $C_5$–$C_8$-cycloalkyl or aryl group which is optionally substituted by $C_1$–$C_6$-alkyl or $C_1$–$C_6$-alkoxy group;

b) reacting the 1,7-dibromoperylene-3,4,9,10-tetracarboxylic diimide formed in step (a) of formula IV

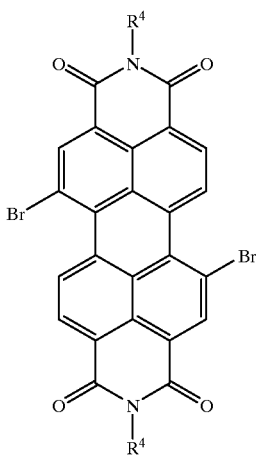

in the presence of an aprotic solvent, a palladium complex as catalyst, a copper salt as a cocatalyst and a base, first with a 1-alkyne of formula Va

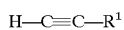  Va and then with a different 1-alkyne of formula Vb

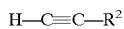  Vb in each case in a molar ratio of from 1:1 to 1:2; and c) hydrolyzing the asymmetric 1,7-disubstituted perylene-3,4,9,10-tetracarboxylic diimide formed in step (b) of formula VI″

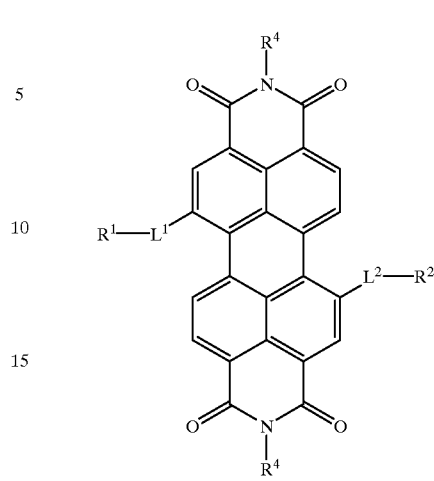

8. The process of claim 7, which further comprises; conducting the reaction of step (a) in the presence of an imidation catalyst.

9. A method of coloring a material, comprising:
   incorporating the compound of claim 1 as a pigment into said material.

10. A method of achieving lazing action, comprising:
    optically exciting the compound of claim 1 as a laser dye thereby achieving lazing action.

11. A method of synthesizing a fluorescent dye, polymeric colorant, pigment or pigment additive, comprising:
    derivatizing the compound of claim 1.

* * * * *